(12) United States Patent
Joshi

(10) Patent No.: US 10,449,263 B2
(45) Date of Patent: Oct. 22, 2019

(54) DEVICES FOR DISINFECTION, DEODORIZATION, AND/OR STERILIZATION OF OBJECTS

(71) Applicant: Microlin, LLC, Salt Lake City, UT (US)

(72) Inventor: Ashok V. Joshi, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 75 days.

(21) Appl. No.: 15/533,653

(22) PCT Filed: Dec. 10, 2015

(86) PCT No.: PCT/US2015/064999
§ 371 (c)(1),
(2) Date: Jun. 7, 2017

(87) PCT Pub. No.: WO2016/094658
PCT Pub. Date: Jun. 16, 2016

(65) Prior Publication Data
US 2017/0368220 A1 Dec. 28, 2017

Related U.S. Application Data

(60) Provisional application No. 62/090,799, filed on Dec. 11, 2014.

(51) Int. Cl.
*A61L 2/20* (2006.01)
*A61L 9/12* (2006.01)
(Continued)

(52) U.S. Cl.
CPC .................. *A61L 9/12* (2013.01); *A61L 2/10* (2013.01); *A61L 2/202* (2013.01); *A61L 2/208* (2013.01);
(Continued)

(58) Field of Classification Search
CPC ... A61L 2/088; A61L 2/10; A61L 2/18; A61L 2/20; A61L 2/202; A61L 2/208;
(Continued)

(56) References Cited

U.S. PATENT DOCUMENTS 6,132,680 A 10/2000 Addy et al.
6,187,266 B1 * 2/2001 Lin .......................... A61L 2/186
422/28

(Continued)

FOREIGN PATENT DOCUMENTS

CN 104016511 9/2014
EP 1382666 1/2004

OTHER PUBLICATIONS

International Search Report and Written Opinion, PCT/US2015/64999, dated Feb. 12, 2016.

*Primary Examiner* — Timothy C Cleveland
(74) *Attorney, Agent, or Firm* — Brian C. Trask

(57) ABSTRACT

A treatment chamber 102 in which an object may be disinfected, deodorized, and/or sterilized. A source 172 of Hydroxyl radicals is arranged to introduce treatment agents, including Hydroxyl radicals, into the chamber 102. Operable sources 172 include nebulizer, Fenton generator, and Hydrogen Peroxide in the presence of nanoparticle catalyst and UV light. Ozone may be applied as an additional treatment agent. A tablet dispenser 128 may optionally be included to introduce additional chemical treatment agents into the chamber 102. The entire treatment device 100A-O may be sized for placement and use at the point-of-use of an object to be sterilized, such as in a hospital to sterilize an endoscope component.

19 Claims, 12 Drawing Sheets

(51) Int. Cl.
   *A61L 2/23* (2006.01)
   *A61L 2/10* (2006.01)
   *A61L 2/22* (2006.01)
   *A61L 9/20* (2006.01)

(52) U.S. Cl.
   CPC .............. *A61L 2/22* (2013.01); *A61L 2/23* (2013.01); *A61L 9/20* (2013.01); *A61L 2202/122* (2013.01)

(58) Field of Classification Search
   CPC .......... A61L 2/22; A61L 2/23; A61L 2202/11; A61L 2202/12; A61L 2202/112; A61L 2202/123
   See application file for complete search history.

(56) References Cited

U.S. PATENT DOCUMENTS

| | | | |
|---|---|---|---|
| 2004/0057868 A1* | 3/2004 | McVey | A61L 2/202 422/28 |
| 2005/0129571 A1* | 6/2005 | Centanni | A61L 2/202 422/31 |
| 2005/0260107 A1 | 11/2005 | Jackson et al. | |
| 2009/0074611 A1* | 3/2009 | Monzyk | A61L 2/02 422/29 |
| 2011/0085934 A1 | 4/2011 | Joshi et al. | |
| 2012/0094887 A1 | 4/2012 | Tanaka et al. | |
| 2012/0263800 A1* | 10/2012 | Berentsveig | A01N 25/06 424/616 |
| 2014/0034961 A1 | 2/2014 | Fujikane et al. | |
| 2014/0143959 A1 | 5/2014 | Job et al. | |
| 2015/0305344 A1* | 10/2015 | Burke | A61L 2/208 424/616 |

* cited by examiner

DEVICES FOR DISINFECTION, DEODORIZATION, AND/OR STERILIZATION OF OBJECTS

PRIORITY CLAIM

This application is a National Phase entry of PCT application Serial No. PCT/US2015/064999, which claims the benefit of the filing date of U.S. Provisional Patent Application Ser. No. 62/090,799, filed 11 Dec. 2014, for "DEVICE AND METHOD FOR OPTIONAL DISINFECTION, DEODORIZATION, AND/OR STERILIZATION", the entire contents of which are hereby incorporated as though set forth herein in their entirety.

TECHNICAL FIELD

This invention relates to apparatus and methods for optionally disinfecting, deodorizing, and/or sterilizing various object(s). Preferred embodiments are structured to promote the presence of hydroxyl radicals inside a treatment zone that holds the object(s).

BACKGROUND

Currently, a wide range of equipment and methods are available to disinfect or sterilize objects and surfaces in residential, industrial, commercial, hospital, hotel, and food processing environments. Exemplary treatment devices for treatment of objects, and methods of use for those treatment devices, are disclosed in U.S. Pat. No. 7,892,486, the entire contents of which are hereby incorporated as a portion of this disclosure by reference. A document disclosing characterization and use of Peroxone as a treatment substance is available on the world wide web at epa.gov/ogwdw/mdbp/pdf/alter/chapt_7.pdf. Although directed generally toward treatment of water, the aforementioned document is also incorporated by reference as a portion of this disclosure.

Unfortunately, the state of the art products and equipment for disinfecting, deodorizing and/or sterilizing are confined to products best suited to use in a commercial or industrial environment, due to increased expense and cumbersome methods and harsh chemicals. In view of the foregoing, what is needed are products, equipment and methods for disinfecting, deodorizing, and/or sterilizing surfaces of objects which are simple to use, less expensive, and more environment friendly

DISCLOSURE OF THE INVENTION

The invention may be embodied to provide a treatment device in which an object may be disinfected, deodorized, and/or sterilized. An exemplary such device includes a first chamber defining a volume in which to receive one or more object to be treated and a source of Hydroxyl radicals configured and arranged to introduce Hydroxyl radicals as a treatment agent inside the first chamber. Desirably, the device is structured to establish a Hydroxyl radical concentration of between about 50 ppm and 10,000 ppm in the first chamber.

A treatment device may also include a source of Ozone structured to introduce Ozone molecules into the first chamber as an additional treatment agent. Sometimes, the treatment device may include a catalyst substance such as Nano Titanium Dioxide structures, or Nano Gallium Nitride structures. Certain treatment devices may include a dispenser structured to dispense a chemical compound into the first chamber to introduce another treatment agent into that chamber. An exemplary such chemical compound includes alkali percarbonate or alkali perborate, or a combination thereof, in tablet form.

A preferred treatment device is structured and arranged to permit operation of the treatment device at point-of-use of objects to be treated. One such treatment device is sized and constructed to permit transporting the treatment device through an opening of about 4 feet in width, and about 6 feet in height.

One operable source of Hydroxyl radicals includes structure configured to urge flow of Hydrogen Peroxide over a catalyst substance in the presence of UV light. An operable source of Hydroxyl radicals includes a Fenton reactor. Another operable source of Hydroxyl radicals includes a nebulizer arranged to introduce a mix of gasses, including nebulized Hydrogen Peroxide and Ozonized air, into the first chamber. Desirably a source of food-grade Hydrogen Peroxide is placed in fluid communication with the nebulizer, wherein concentration of the Hydrogen Peroxide is between about 5% and about 50% by weight. Sometimes Hydrogen Peroxide also contains Silver Nitrate or Silver Citrate between about 0.05% to about 5% by weight to introduce additional treatment agents into a chamber.

Certain embodiments include a source of Hydroxyl radicals that is configured to produce Hydroxyl radicals exterior to the first chamber. Other embodiments may include a source of Hydroxyl radicals that is configured to produce Hydroxyl radicals in the interior of the first chamber.

Certain treatment devices are particularly structured to permit treating both inside and outside surfaces of tubular elements having an extended length. One such treatment device includes a second chamber structured to communicate treatment agents or gasses to the first chamber through a lumen in a tubular object to be treated. Another such treatment device includes a Hydrogen Peroxide bath disposed inside the first chamber and an Ozone source configured and arranged to bubble gas containing Ozone through the bath to permit bubble travel through a lumen of an object to be treated inside the first chamber. Another such treatment device includes a vacuum disposed in communication through a first flow control device to the first chamber, and a source of Hydroxyl radicals disposed in communication to the first chamber through a second flow control device. An exemplary flow control device may be embodied as a valve.

BEST MODES FOR CARRYING OUT THE INVENTION

Figure 1:
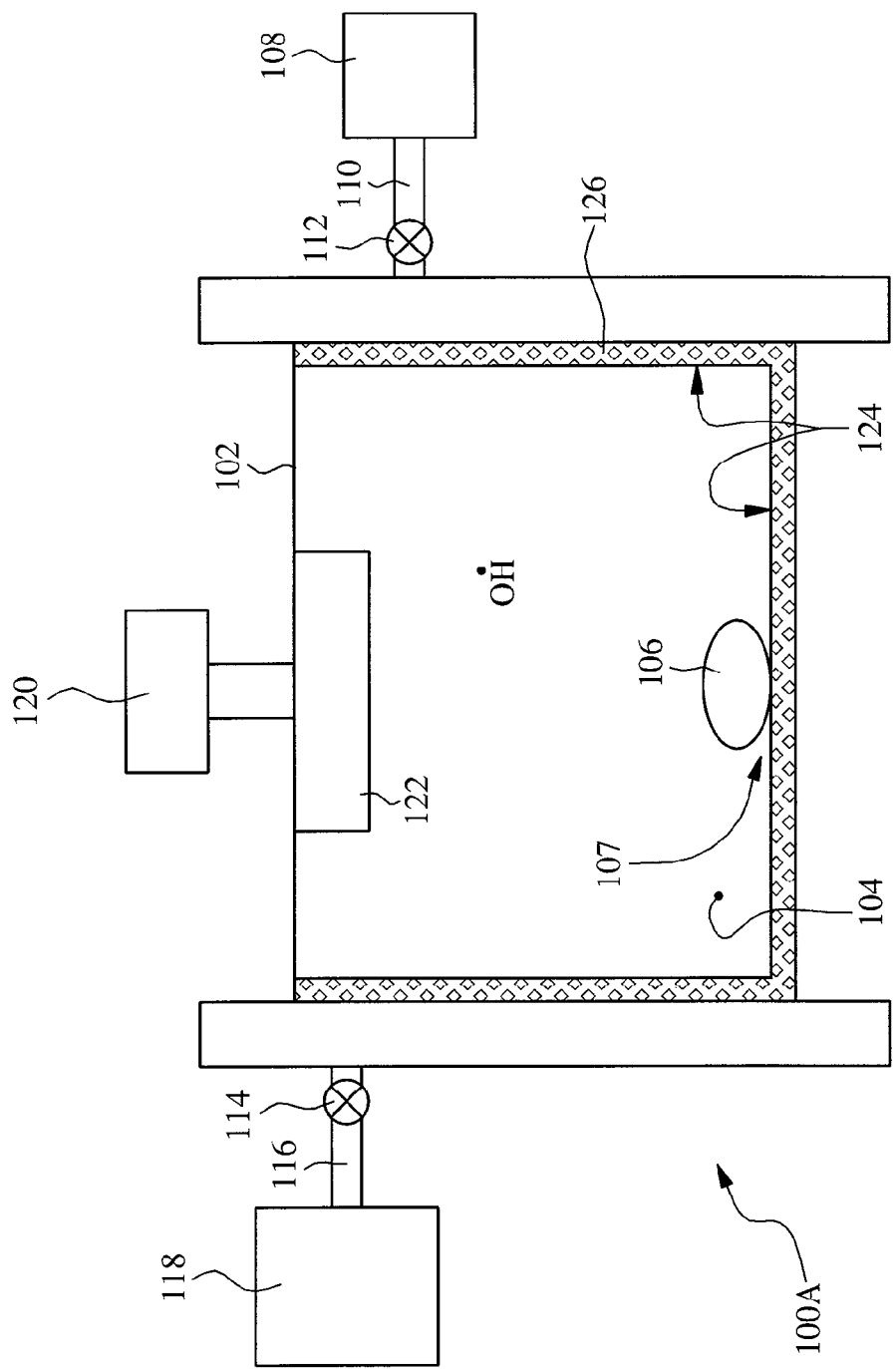
FIG. 1 is a pictorial view in elevation of a first device structured according to certain principles of the instant invention.

The device, generally 100A, indicated in FIG. 1 includes a chamber 102 defining an internal volume 104 sized to contain one or more object 106 for which disinfection, deodorization, and/or sterilization is desired. An anatase Titanium Oxide Nano needle array plate can be used as a platform 107 on which object 106 can be placed. Air handling unit 108 is adapted to introduce air through conduit 110, past valve 112, and into the chamber volume 106. An operable air handling unit 108 may include a fan, or a compressor, pump, and the like. The chamber atmosphere may be exhausted by opening valve 114 to permit air flow through conduit 116 for treatment (if required), by optional exhaust treatment unit 118 prior to discharge chamber's atmosphere to the general, or outside atmosphere. A workable catalyzing exhaust system 118 for Ozone destruction is commercially available. A plurality of workable exhaust treatment or processing systems 118 may be found on the world wide web by searching the term "ozone and hydroxyl radical destruct unit".

With continued reference to FIG. 1, an electronic control and power system 120 may be coupled to an ultraviolet (UV) light source 122 that is disposed to direct UV radiation inside the chamber 102, in accordance with known construction techniques. Desirably, the UV light 122 is capable of generating Hydroxyl radicals at a rate sufficient to perform treatment of an item 106 in a reasonable amount of time. A reasonable amount of time for a disinfecting treatment is believed to be on the order of 5-10 minutes, and desirably is less than that. A workable Hydroxyl radical generation rate is sufficient to accomplish about 50 ppm to 10,000 ppm, or so, in a treatment zone.

As illustrated in FIG. 1, UV light is directed toward one or more surface 124 inside the chamber 102 that has catalyst properties to enhance a chemical reaction that produces Hydroxyl radicals. It is within contemplation that surface 124 may be provided by a coating 126, or may simply be the surface of a substance. A workable coating 126 may be formed by way of a conventional manufacturing process, such as powder coating, vapor deposition, and the like. For non-limiting examples, any or all of the wall(s), floor, shelve(s), one or more divider, removable panel, and ceiling may be coated with a catalyst substance. On the other hand, a catalyst substance may be provided in an open container to receive UV radiation on an exposed surface of the substance.

Currently preferred catalyst materials include Nano Titanium Oxide and Nano Gallium Nitride wires, tubes, or other structures. A workable catalyst may comprise Nano tin Oxide or Nano ZnO, CdS, ZnS, SiC or $Cu_2O$ or any inert material with band gap of 3.0±1 eV as replacement, or supplement to Nano Titanium Oxide or Nano Gallium Nitride structures.

The treatment time produced by a given treatment device, such as device 100A, is a function that generally includes the following variables: radiation intensity; amount of radiated surface of catalyst; % relative humidity; temperature; and chamber volume. The addition of a catalyst is a significant improvement to reduce treatment times over a comparable device that lacks the catalyst. Although the equation describing the chemical reaction does not change, the rate of the reaction to generate Hydroxyl radicals is greatly increased by presence of an effective catalyst, as well as Alkali percarbonates or borates. Given a first treatment device lacking a catalyst, treatments times for that device are expected to decrease by perhaps 20-50%, or so, when a suitable amount of irradiated surface area of a workable catalyst is added.

Preferred embodiments structured according to certain principles of the invention are directed toward enhancing, or even maximizing, the generation of Hydroxyl radicals, since Hydroxyl radicals are 15 times more potent than Ozone. In use of the exemplary device 100A, the object 106 to be treated is placed inside the chamber 102, then the chamber 102 is closed and the UV light 122 is turned on. Ambient air with controlled humidity is then forced by air handling unit 108 into the chamber 102 through the open inlet valve 112. A workable range in humidity is believed to be between about 40% to about 90%. Exhaust valve 114 may be initially open to permit filling the chamber at ambient pressure, or closed for pressurized operation. In any case, exhaust valve 114 is generally closed during the treatment process.

UV light in the chamber, augmented by the Nano catalyst material, in combination with controlled Humidity may form Hydroxyl radicals and Ozone to deodorize, disinfect, and/or sanitize the object 106. It is desirable that the placement of UV light or lights is such that at least some light falls on Nano catalyst to generate antimicrobial radicals and gasses. It is within contemplation that a heat source (not illustrated) may sometimes be included in a device to raise the internal chamber temperature during treatment. The object 106 remains inside chamber 102 until a desired amount of treatment is applied. Required treatment time increments increase to produce deodorization, disinfection, and sterilization, respectively. Subsequent to treatment of object 106, chamber gasses may be exhausted to atmosphere through an optional exhaust treatment unit 118.

Figure 2:
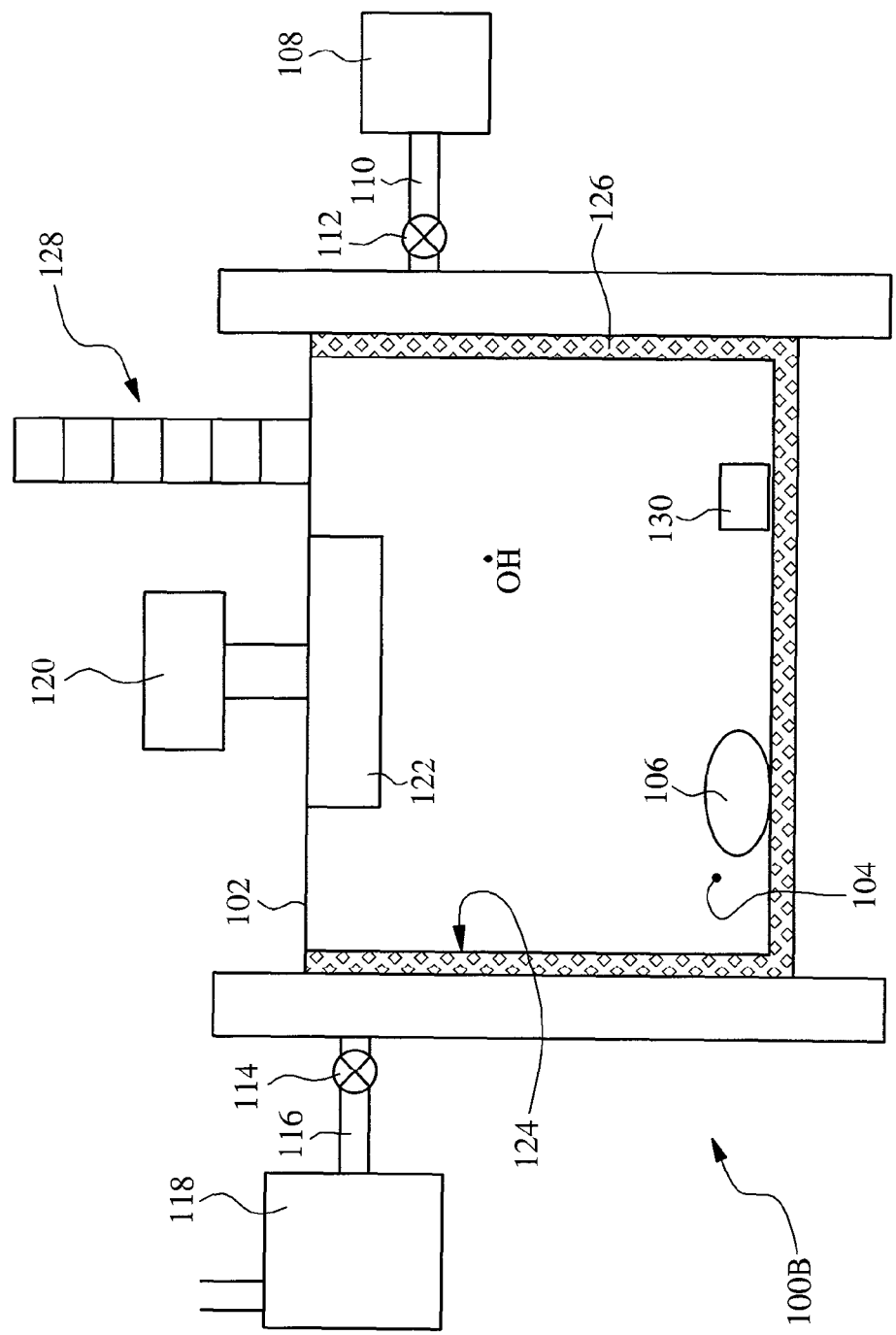
FIG. 2 is a pictorial view in elevation of a second device structured according to certain principles of the instant invention.

Device 100B, illustrated in FIG. 2, includes similar structure to that present in embodiment 100A, and is numbered accordingly. Additionally, device 100B includes a tablet dispenser, generally 128, structured to optionally dispense one or more tablet 130 as desired into the chamber 102. Tablet dispensing may occur at any desired time during a treatment process, and may be done multiple times. A currently preferred tablet 130 includes, or consists of, one or more chemical or chemical compound that promotes production of hydroxyl radicals to reduce required treatment times for a given treatment effect. A tablet 130 is desirably dispensed to be positioned in the path of UV light. Workable tablets include alkali percarbonate or alkali perborate, or a combination thereof. Treatment compounds used in certain embodiments may sometimes also include Silver nitrate, Silver citrate, and Benzyl alcohol.

Figure 3:
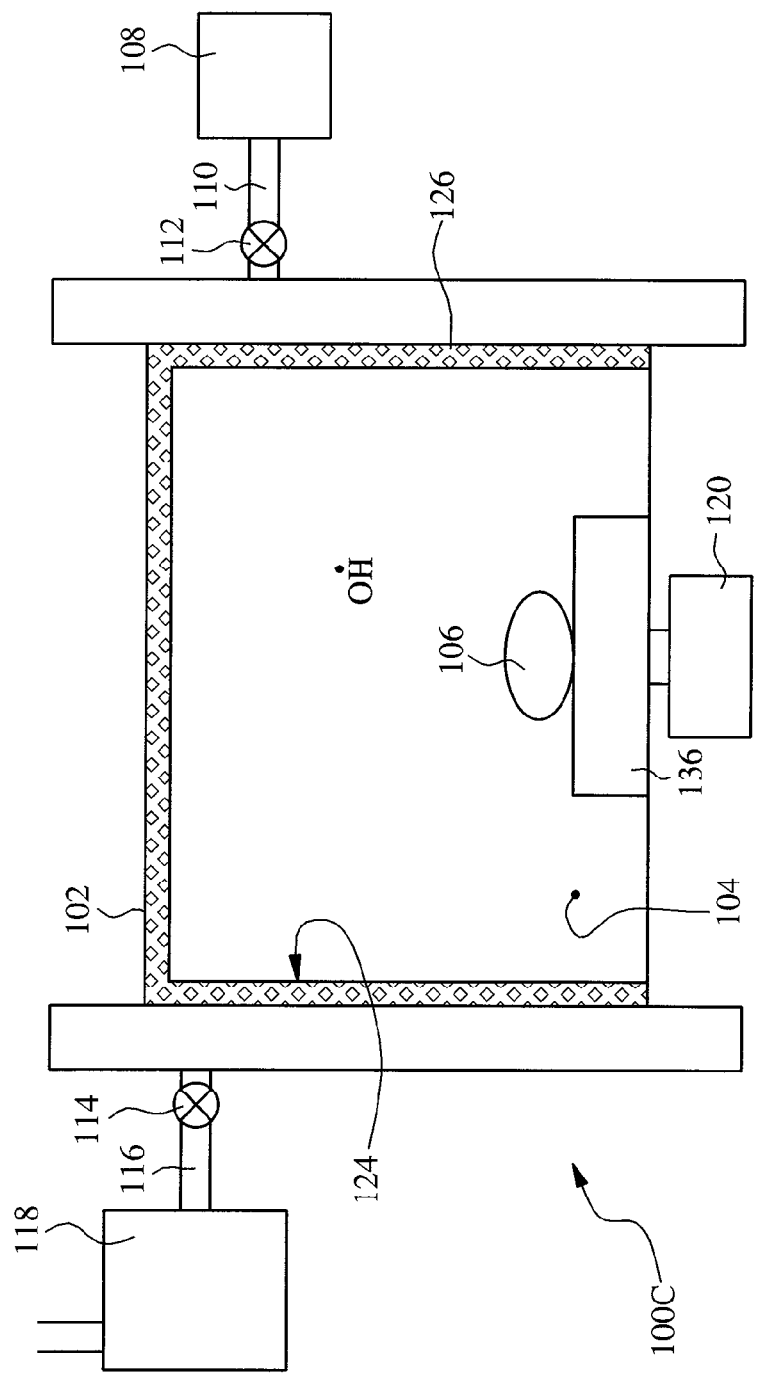
FIG. 3 is a pictorial view in elevation of a third device structured according to certain principles of the instant invention.

The device 100C in FIG. 3 also includes similar structure to that present in embodiment 100A, and is numbered accordingly. Device 100C includes a surface corona unit 136, for generating a corona inside the chamber 102. The location of corona unit 136 can be chosen depending on the application. All other features are the same as in FIG. 1, except there is no UV light. The corona unit 136 is illustrated as being operated by an electronic control system 120. Hydroxyl radicals and ozone are generated when air with controlled humidity is introduced in the chamber 102. The humidity and oxygen in the air along with corona discharge (and an optional Nano catalyst like $TiO_2$ or GaN) create Hydroxyl radicals and ozone which treat the object 106 to either deodorize, disinfect or sterilize depending on time of the treatment, strength of corona discharge and circulation of air in the chambers to generate required concentration of Hydroxyl radicals and ozone.

Figure 4:
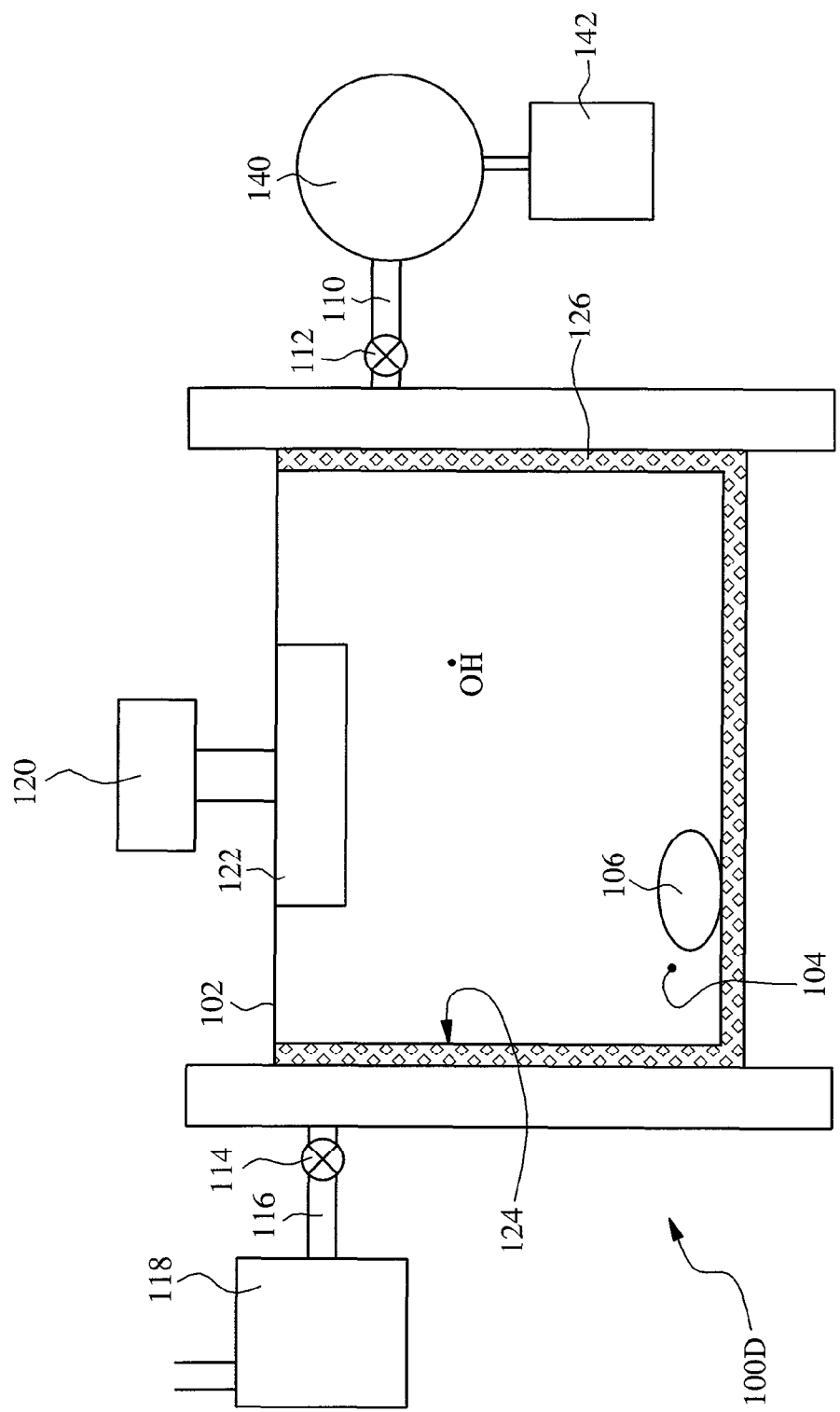
FIG. 4 is a pictorial view in elevation of a fourth device structured according to certain principles of the instant invention.

FIG. 4 shows another embodiment of a treatment device, generally 100D. In device 100D, the chamber 102 is fitted with all the features shown in FIG. 1, except that instead of air handling unit 108, a hydrogen peroxide nebulizer 140 is connected to the chamber 102 to deliver a vapor of Hydrogen Peroxide ($H_2O_2$) into the chamber volume 104 during the treatment. Hydrogen Peroxide, UV light and an operable catalyst (such as Nano $TiO_2$ tubes or GaN Nano wires) together create a high concentration of Hydroxyl radicals and Ozone together to treat the object. The strength of $H_2O_2$, and UV light distribution along with quality of the Nano tube or wire coatings of $TiO_2$ or GaN will determine the time of the treatment required to deodorize, disinfect, and/or sterilize the object 106.

A preferred feedstock 142 for nebulizer 140 includes food-grade Hydrogen Peroxide having a concentration by weight percent of $H_2O_2$ vs. $H_2O$ between about 5% to about 50%. Sometimes, the Hydrogen Peroxide may be in a stabilized condition, particularly in stronger concentrations. For example, Magnesium Sulfide ($MgSO_4$), or Sodium Stannate ($Na_2SnO_3$) may be combined with Hydrogen Peroxide. Also, Silver Nitrate ($AgNO_3$) or Silver citrate may be added to the Hydrogen Peroxide between about 0.05% to about 5% by weight to greatly enhance the killing or treatment power of the resulting treatment agent when introduced into a chamber 102.

Figure 5:
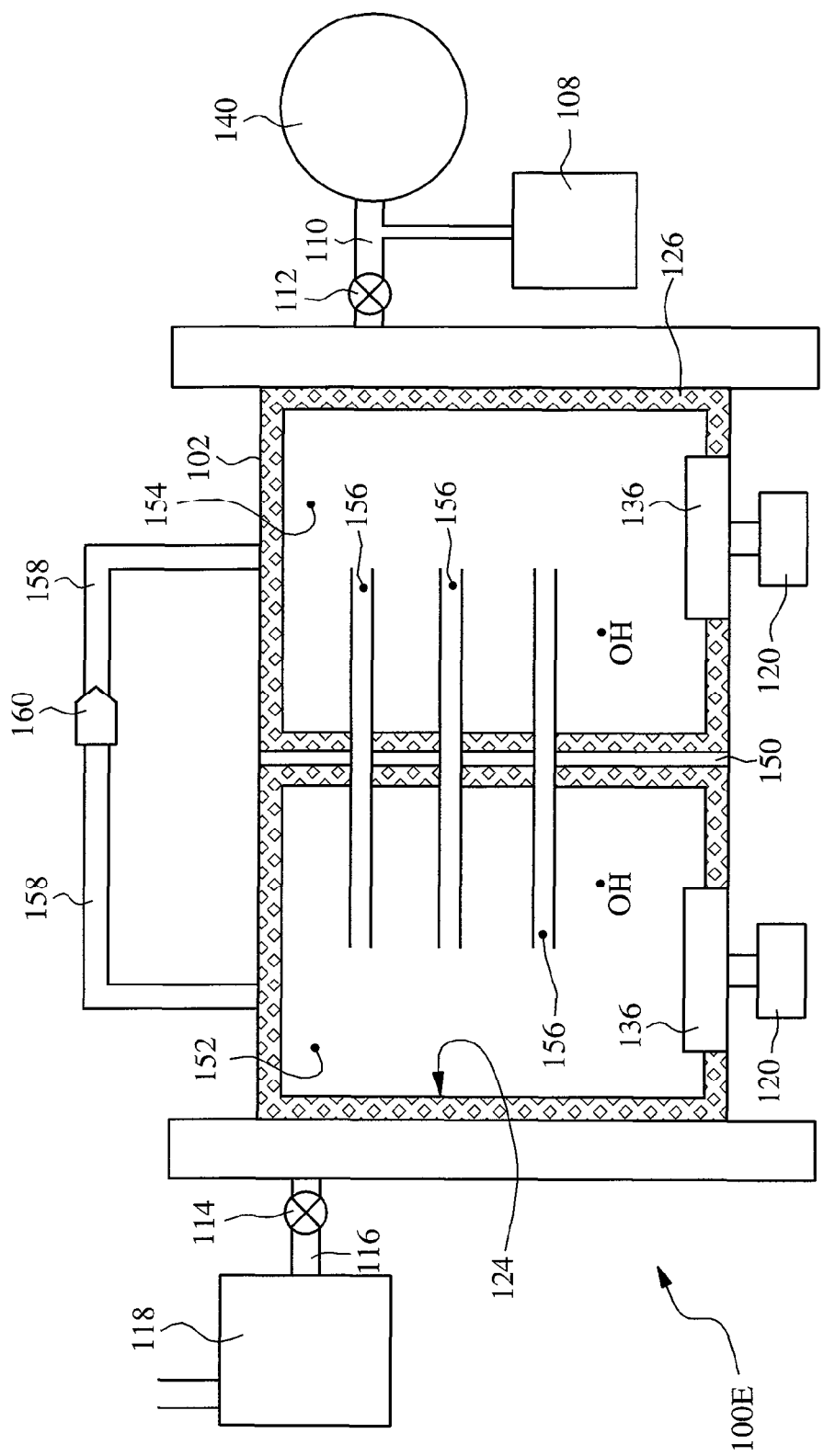
FIG. 5 is a pictorial view in elevation of a fifth device structured according to certain principles of the instant invention.

The treatment device illustrated in FIG. 5, generally 100E, is adapted to treat lumen, or tubes, from both inside and outside. In embodiment 100E, the treatment chamber 102 has two compartments with a divide 150 between them. The tubes to be treated are placed as shown to communicate gasses between left side compartment 152 and right side compartment 154. The illustrated embodiment including a divider 150 is intended to convey a general idea about control of treatment gasses to direct their flow over, and through, a lumen or tube 156, thereby to treat all surfaces of that tube 156. Of course, it is recognized that the illustration leaves a central exterior of a lumen 156 (passing through a divider 150), that is potentially untreated by contact with treatment gasses. However, one of ordinary skill in the art will appreciate alternative structural arrangements effective to perform the desired control and application of treatment gasses.

Either, or both, of right side 154 and left side 152 of the chamber 102 may include one or more corona discharge unit 136. Desirably, radiation from a corona discharge unit 136 is directed to fall on a surface 124 that carries a catalyst to promote formation of Hydroxyl radicals and Ozone. A plurality of corona discharge units 136 may be controlled or powered by a single control unit 120, or units 136 may individually be controlled by a local control unit 120 (illustrated). By way of example the right chamber 154 can be charged with hydrogen peroxide vapor and humidified air (e.g. by way of nebulizer 140 and air handling unit 108). Treatment gasses communicate between chamber sides 152, 154 through lumen 156. A corona discharge unit 136 (disposed in either the right chamber 154 and/or left chamber 152) interacts with hydrogen peroxide vapor in admitted humid air to generate a mixture of treatment gasses, including Hydroxyl radicals and Ozone. Treatment gasses pass through the lumen or tubes 156 from right chamber 154 to left chamber 152, and then communicate through recirculation conduit 158 under influence of fan system 160 for reintroduction into the right chamber 154. Consequently, both interior and exterior surfaces of the lumen 156 are bathed in treatment gasses. When the treatment process is complete, exhaust valve 114 may be opened, and the exhaust from the chamber 102 can be treated in an optional exhaust treatment unit 118 to exhaust only water and $CO_2$ into the outside atmosphere.

Figure 6:
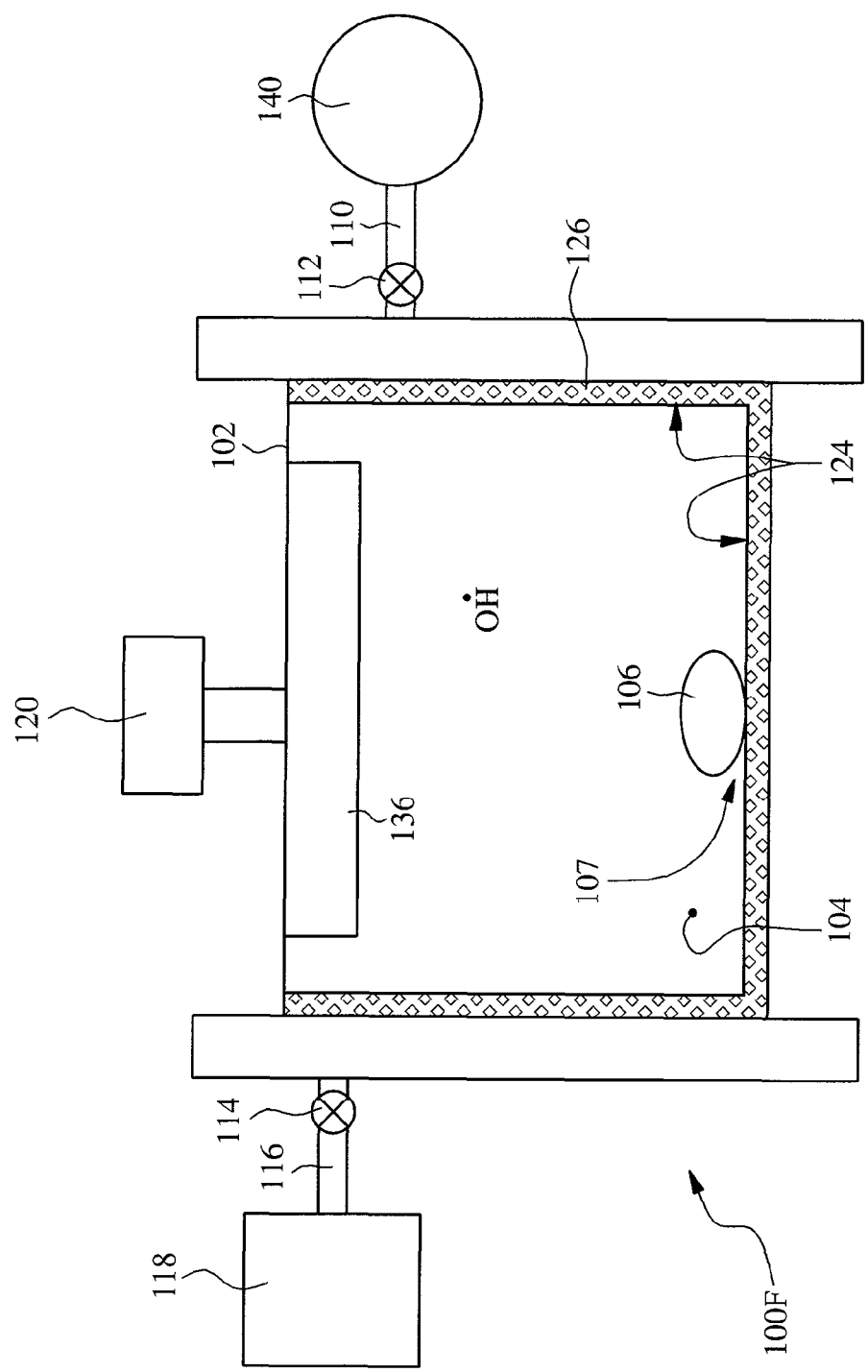
FIG. 6 is a pictorial view in elevation of a sixth device structured according to certain principles of the instant invention.

The treatment device, generally 100E, in FIG. 6 illustrates a similar embodiment to that depicted in FIG. 4, except that instead of a UV light fixture in the treatment chamber 102, a corona discharge unit 136 is mounted in the treatment chamber 102. When the Hydrogen peroxide nebulizer 140 delivers a vapor of hydrogen peroxide with humidified air into the chamber 102, the corona discharge unit 136 and Nano catalyst tubes and wires generate Hydroxyl radicals and Ozone in the chamber for treatment of one or more object 106.

Figure 7:
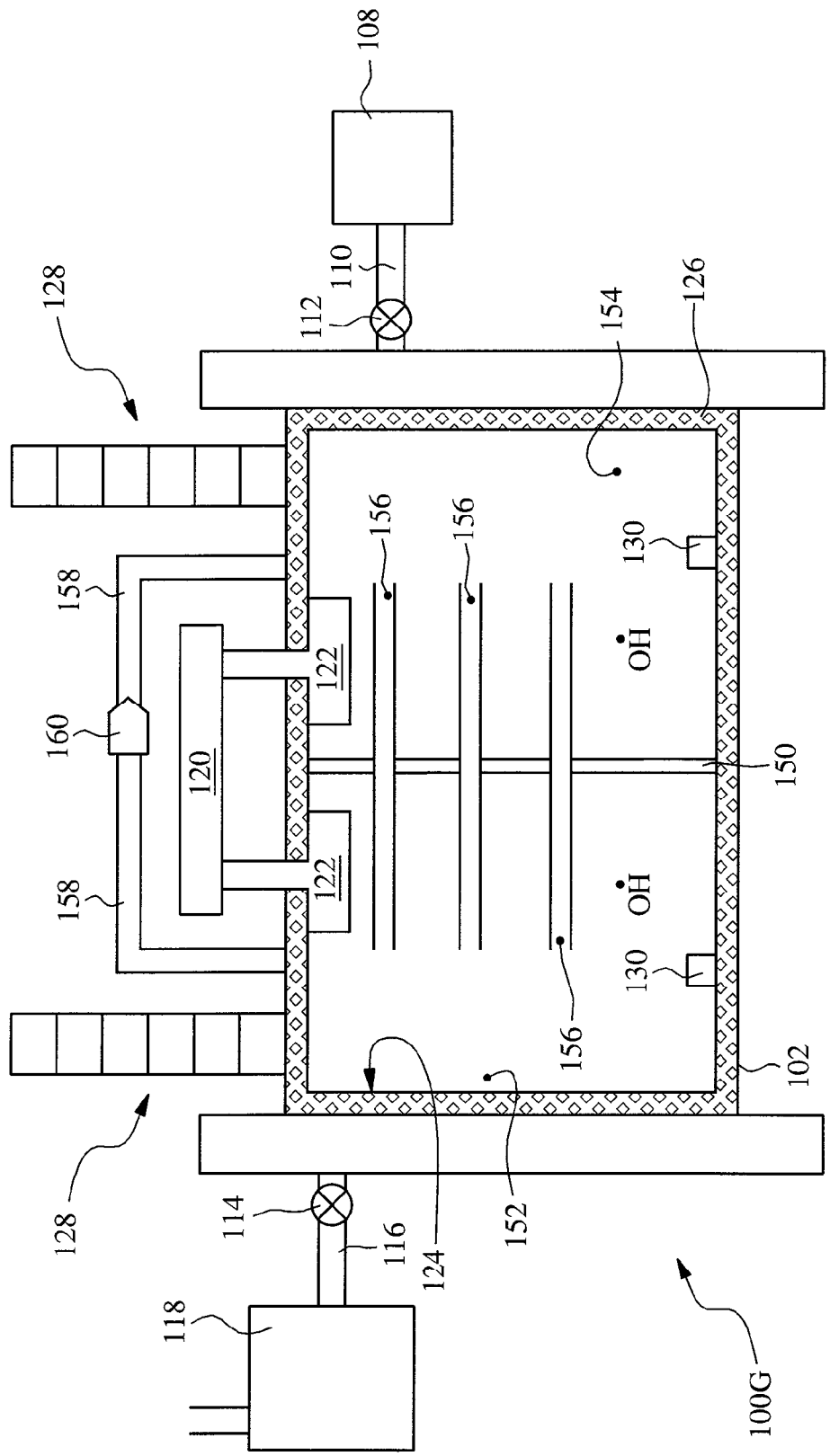
FIG. 7 is a pictorial view in elevation of a seventh device structured according to certain principles of the instant invention.

FIG. 7 shows a two compartment apparatus, generally 100G, for treating lumen and tubes 156 similar to apparatus 100E shown in FIG. 5, except that instead of corona discharge units, each chamber is fitted with a UV light fixture 122 as well as a tablet dispenser, generally 128. Currently preferred tablets 130 include Alkali percarbonate or Alkali perborate compounds. As illustrated, peroxide nebulizer 140 in device 100E has been replaced with an air handling unit 108. In exemplary operation of this embodiment, the right chamber 154 can be held at a higher pressure than that inside left side chamber 152. When the antimicrobial elements like Hydroxyl radicals and Ozone form, they travel over and through the lumen 156 and treat the outside and inside of lumen and tubes 156, respectively. When the treatment gasses exit through the tube 156 to the left side chamber 152 (moving from higher toward lower pressure), the gasses may be directed to circulate through recirculation conduit 158 to right side chamber 154 under influence of a fan circulation system 160. Once the treatment is finished, then the exhaust gases can optionally be treated by opening exhaust valve 114 to pass gas contents of chamber 102 for treatment in an optional exhaust treatment unit 118 before exhausting harmless $CO_2$ and water vapor to the general atmosphere.

Figure 8:
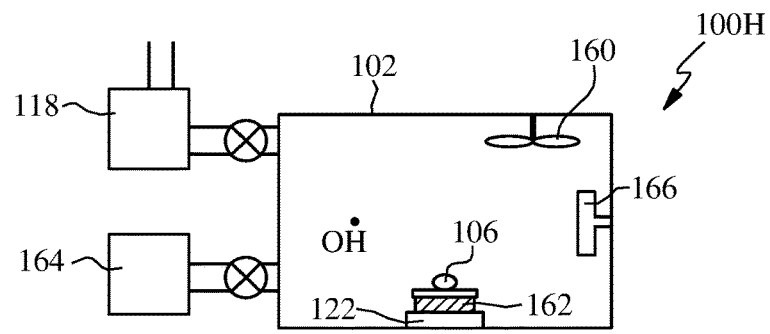
FIG. 8 is a pictorial view in elevation of an eighth device structured according to certain principles of the instant invention.

The apparatus 100H in FIG. 8 illustrates a treatment chamber 102 with a fan or gas circulation system 160 to circulate moist gasses inside the chamber 102. An object 106 to be treated is placed in the chamber 102, and a chemical compound 162 (such as sodium percarbonate), is irradiated by a UV light source 122 to generate hydroxyl radicals. A catalyst (not illustrated) may also be included inside the chamber to enhance hydroxyl radical production. Optionally, a vacuum device 164 may be applied to the chamber prior to, and/or during, treatment to enhance treatment efficacy. Again, the exhaust is typically treated to destroy the hydroxyl radicals (e.g., in exemplary catalyzing exhaust system 118), before emission into the atmosphere. Additional efficacious elements may optionally be included, such as a heating device 166 to heat the treatment environment, or any other device operable to impart additional disinfection, deodorization, or sterilization treatment to an object 106.

Figure 9:
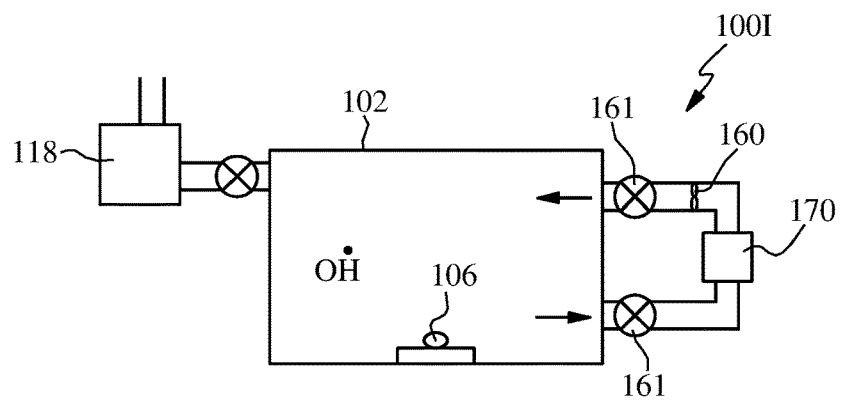
FIG. 9 is a pictorial view in elevation of a ninth device structured according to certain principles of the instant invention.
Figure 10:
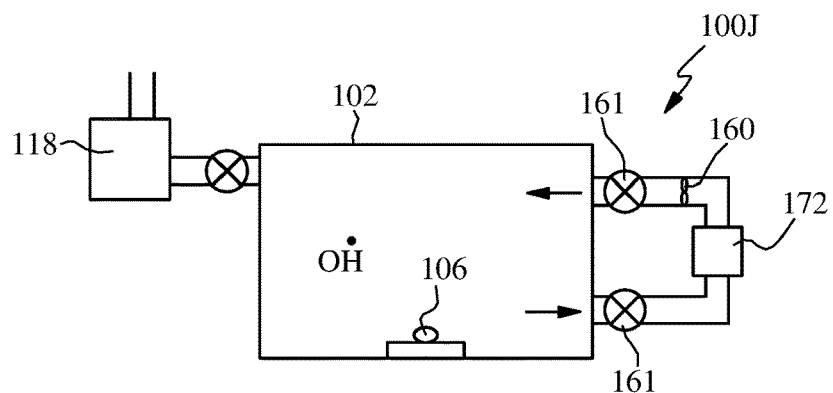
FIG. 10 is a pictorial view in elevation of a tenth device structured according to certain principles of the instant invention.

The apparatus 100I in FIG. 9 illustrates connection of a Fenton reactor 170 to introduce hydroxyl radicals into a treatment chamber 102. As is understood by one of ordinary skill, embodiments may include provision for movement of gasses, including gas circulation system 160. A circulation system 160 may include various elements, including one or more valve 161, pump, fan, damper, conduit, and the like. The well-known Fenton reaction generates Hydroxyl radicals using an Iron compound as a catalyst. One aspect of the present invention includes a new use of a Fenton reactor to introduce Hydroxyl radicals into, and sometimes re-circulate through, the treatment chamber using a simple gas circulation system 160 and recirculation conduits. The apparatus 100J in FIG. 10 illustrates a similar concept, but more broadly. That is, any source 172 capable of generating hydroxyl radicals may be employed to introduce those radicals into a treatment chamber 102.

Exemplary Fabrication of Titanium Dioxide Nanotubes ($TiO_2$-NTs)

Figure 11:
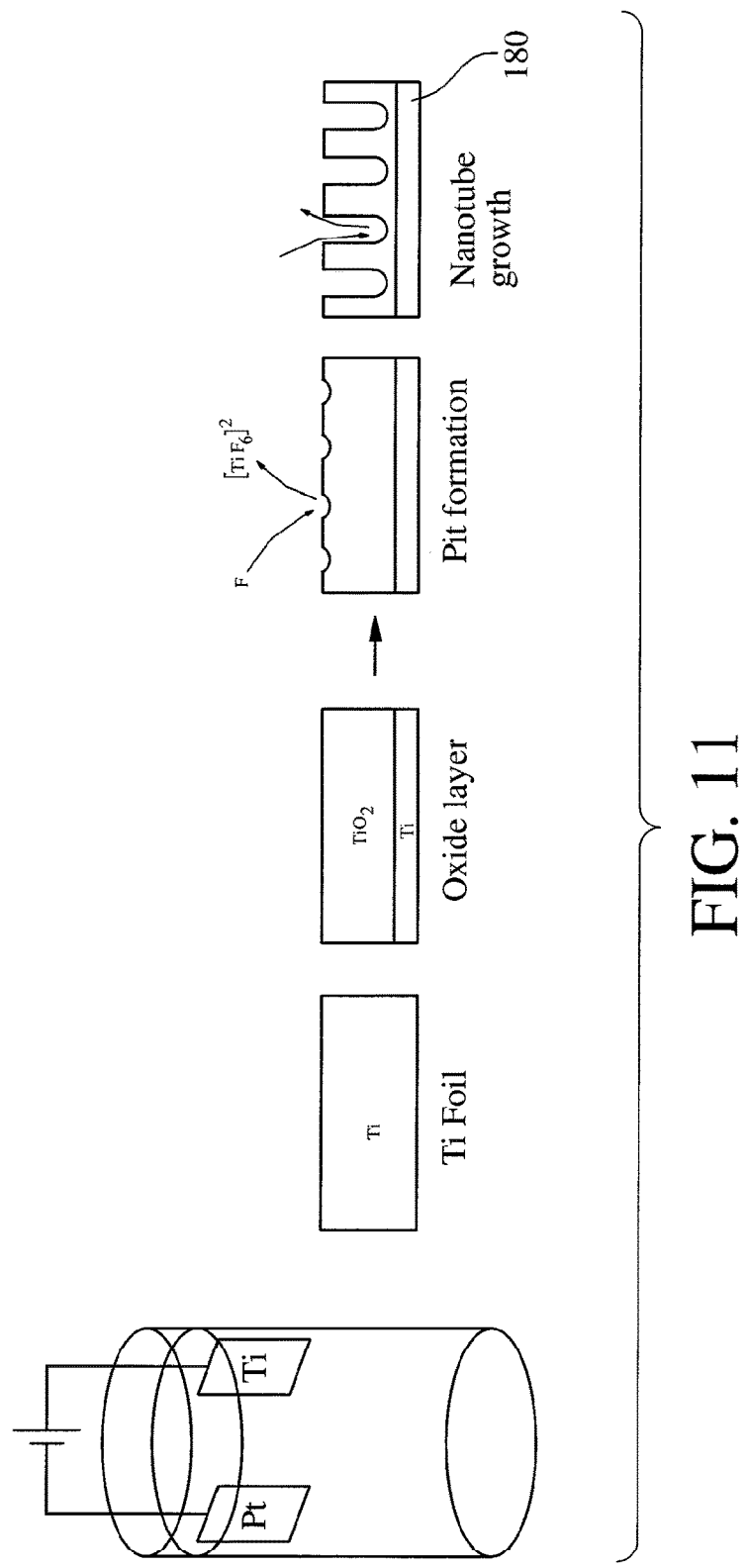
FIG. 11 illustrates a preferred method for fabrication of a workable catalyst according to certain principles of the instant invention

A plurality of fabrication methods to produce Titanium Oxide NanoTubes ($TiO_2$-NTs) have been developed in the last couple of decades. With reference to FIG. 11, an ethylene glycol (EG) fabrication method has recently been developed, which has great benefits on strength, regularity, and homogeneity of nanotubes. $TiO_2$-NTs are generated through several steps of anodization in the mixture of EG, water, and ammonium fluoride ($NH_4F$). Overall reaction (anodization) is performed in EG solution with proper potential flow. At first, an titanium dioxide layer is generated on the surface of pure titanium metal foil. Then, pit formation on the $TiO_2$ surface occurs. Fluoride ($F^-$) in electrolyte binds to $Ti_4^+$ to make a soluble $[TiF_6]^{2-}$ during anodization. Pit depth is determined by anodization time. The final shape of the hole (or pit) looks tubular in form, and tube length and diameter are ~2 um and 80 nm, respectively. $TiO_2$-NTs have benefits on: large surface area, biocompatibility (less toxic), strength, flexibility, conductivity, and photocatalysis for $H_2$ generation.

A foil substrate 180 that carries NanoTubes, such as described above, can easily be applied to a panel for insertion into, or inclusion in, a multipurpose device, such as any of devices 100A-O. The panel can be a structural member of the chamber, such as a floor, ceiling, divider, or wall. Alternatively, the panel may be embodied as a non-structural element, such as a removable element; perhaps even an element that may be variously located in a chamber to accommodate one or more particular object and radiation source. A foil element 180 may be incorporated in operable association with a source of Hydroxyl Radicals.

Figure 12:
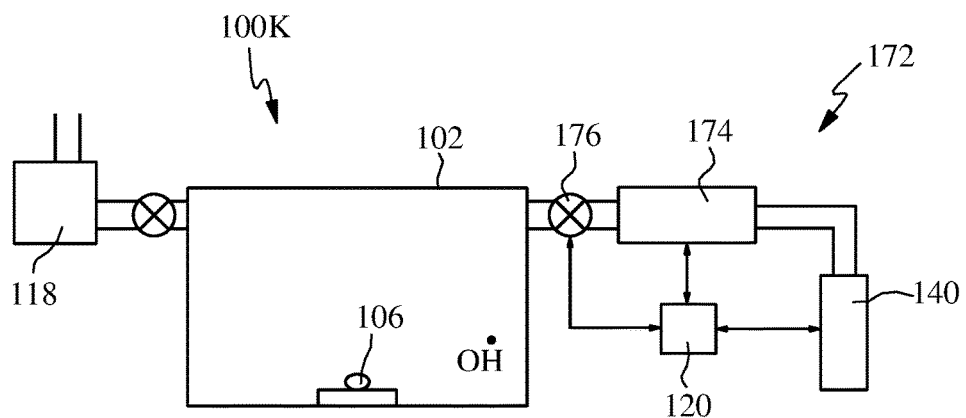
FIG. 12 is a pictorial view in elevation illustrating certain optional details of a device such as that shown in FIG. 10.

FIG. 12 illustrates an example of a workable source of hydroxyl radicals, generally indicated at 172. The alternative treatment device 100K includes provision for exhausting the gas from the treatment chamber 102 through a Hydroxyl radical destruction device 118. The illustrated Hydroxyl Radical source 172 in FIG. 12 includes a Hydrogen Peroxide nebulizer 140 communicating through an Ozone source or generator 174 (such as the illustrated UV tube), and a flow control device 176 (such as the illustrated valve), to the treatment chamber 102. A power and control assembly 120 is structured to operate the nebulizer 140, Ozone generator 174, and flow control device 176 effective to introduce Hydroxyl Radicals into the chamber 102. An operable flow control device 176 includes a one-way valve. Gasses flowing through the Ozone source 174 generate Ozone, which also is applied as a treatment agent inside the chamber 102.

Figure 13:
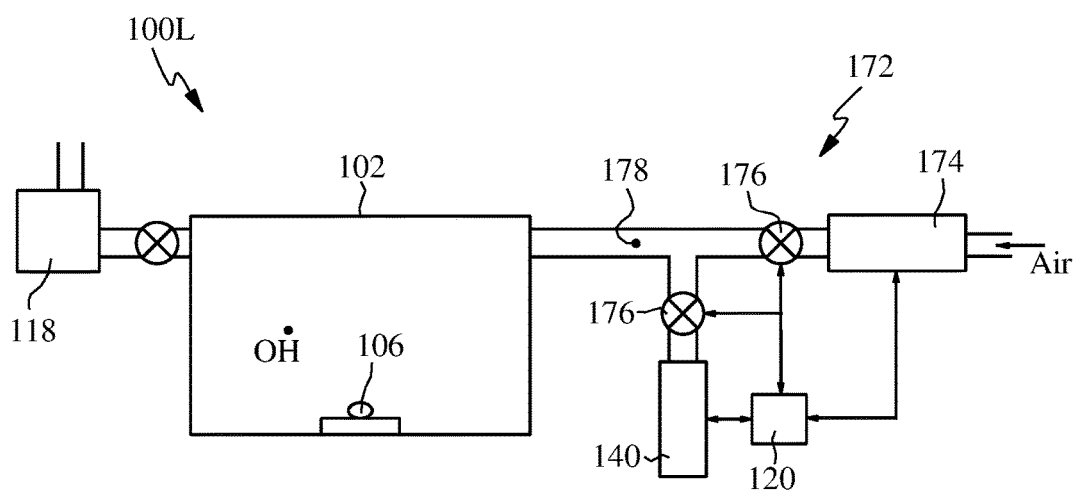
FIG. 13 is a pictorial view in elevation illustrating certain optional details of a device such as that shown in FIG. 10.

FIG. 13 illustrates another example of a workable source of hydroxyl radicals, generally indicated at 172. Comparing FIGS. 12 and 13 illustrates how gas flow and generation of Hydroxyl Radicals may be controlled in alternative ways to generate treatment agents (including Hydroxyl Radicals) for application to treat an object 106 inside a chamber 102. In FIG. 13, Ozone from Ozone generator 174 is mixed with misted Hydrogen Peroxide prior to introduction of the mixed treatment agents into the chamber 102. Production of Hydroxyl Radicals may begin in the conduit 178 and continue inside the chamber 102.

Figure 14:
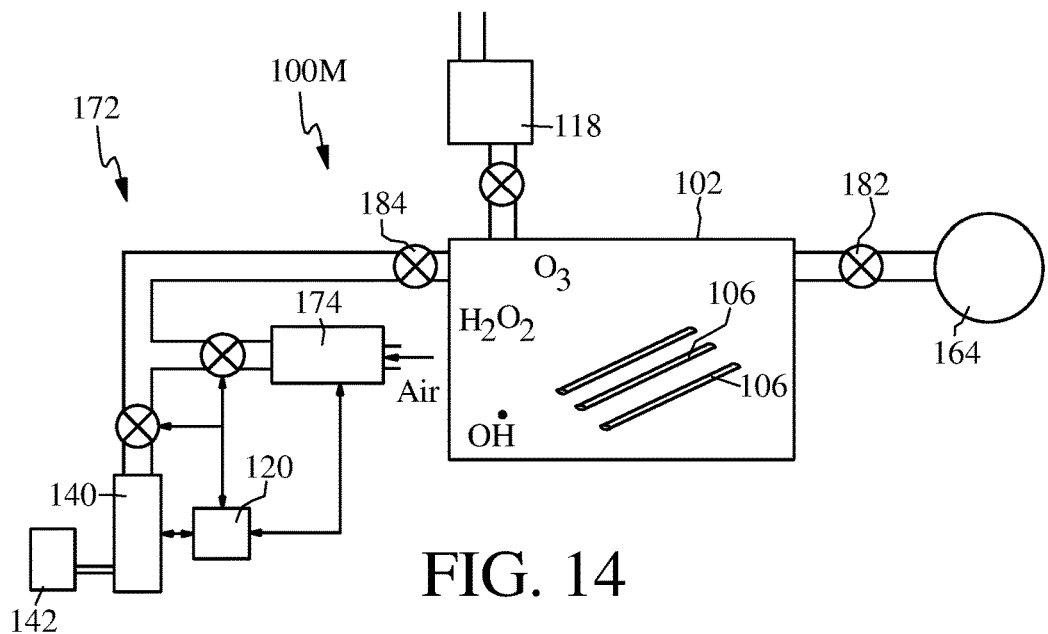
FIG. 14 illustrates another embodiment according to certain principles of the invention, and particularly adapted for treating lumen.

With reference now to FIG. 14, the embodiment generally indicated at 100M includes a vacuum 164 in variable communication through valve 184 to chamber 102. A source of Hydroxyl Radicals 172 is also in variable communication with chamber 102 through valve 184. For purpose of this disclosure, elements discussed in connection with alternative embodiments are similarly numbered to reduce repetition of disclosure. In use, valve 184 is closed, valve 182 is opened, and vacuum 164 is applied to empty the chamber 102 of atmosphere. Then, valve 182 is typically closed, and valve 184 is opened to introduce treatment agents including Hydroxyl Radicals, into the chamber 102 to treat one or more object 106.

Figure 15:
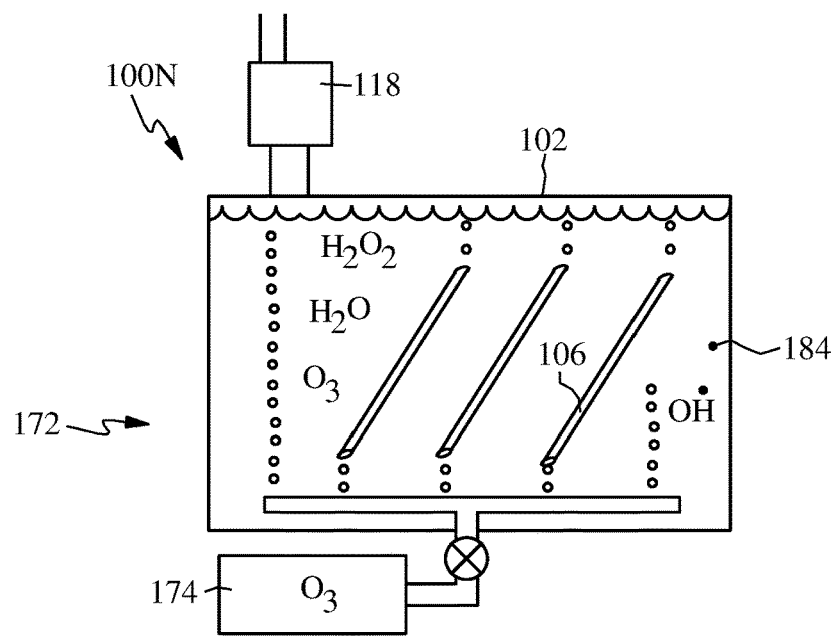
FIG. 15 is another embodiment generally similar to the embodiment in FIG. 14.

Turning now to FIG. 15, the embodiment indicated generally at 100N includes a Hydrogen Peroxide bath 184 inside the chamber 102. One or more object 106 is placed into the bath 184, and then Ozone is introduced to the bath 184 to form Hydroxyl Radicals. As illustrated, it can be advantageous for the Ozone to bubble up through the bath 184 and also travel through one or more lumen of an object 106. Desirably, the bath 184 includes food-grade Hydrogen Peroxide in a weight percent between about 5% and about 50%.

Embodiments structured in harmony with 100N can be sized sufficiently small as to be located for treatment use at point-of-use for objects that must be sterilized. For example, an embodiment similar to 100N can be provided at a hospital to sterilize one, several, tens, or several tens of endoscope components at a time. A chamber may be sized to fit through doorways of conventional size, such as about 4 feet in width and 6 feet in height. A workable chamber 102 may be embodied with a rectangular base having length and width each sized between about ½ to about 2, 3, or 4 feet, and height between about ½ to about 1, 2, 3, or 4 feet. A length or width can be up to 5 feet, 6 feet 7 feet, 8 feet, or more. The height may sometimes be up to 6 feet, 8 feet, 10 feet, or more. In contrast, commercially available sterilizers are structured for mass sterilizing hundreds, thousands, or more, endoscope components at one time. There are many structural differences, including scale of size parameters, between available commercial embodiments and embodiments structured in harmony with 100N. Embodiments according to certain principles of the invention are not constrained to any particular shape. For example, a chamber may be spherical, or other non-rectangular shape.

Figure 16:
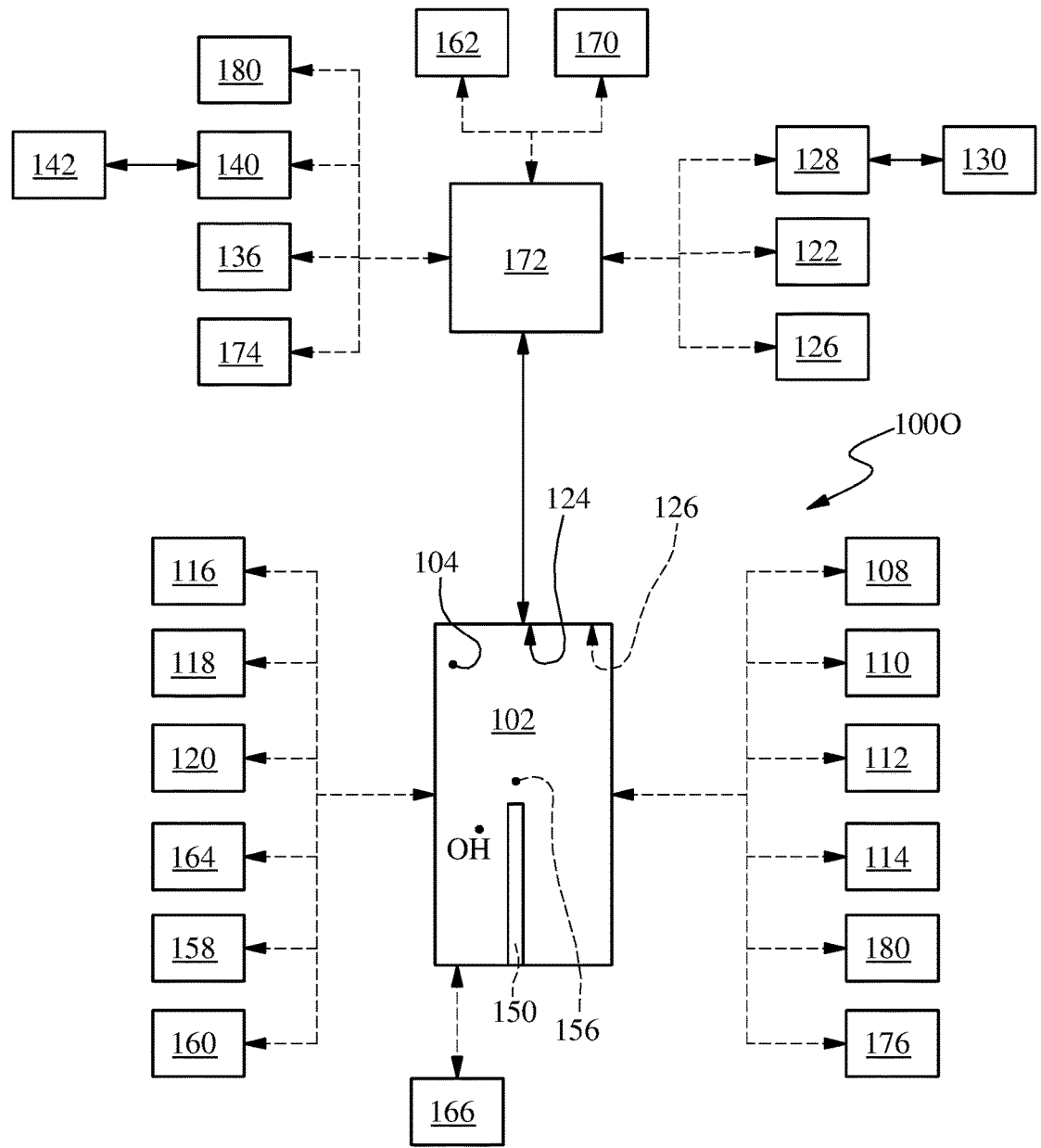
FIG. 16 illustrates a generalized embodiment structured according to certain principles of the invention.

It will also be appreciated by one of ordinary skill that individual elements in any of the various FIGs. may be isolated, extracted, and combined as desired to form alternative combinations and embodiments within the ambit of the instant invention. That is, as illustrated by the embodiment generally indicated at 100O in FIG. 16, efficacious elements may be extracted from any of the alternative embodiments disclosed in this document to mix-and-match and thereby form alternative embodiments of a workable treatment device compared to those that have been explicitly illustrated. Elements are not necessarily mutually exclusive based upon illustration, or not, in any of the FIGs.

In summary, an apparatus structured according to certain principles of the present invention may comprise the use of radiation (such as a UV light, or surface corona discharge unit); a catalyst (such as Nano tubes, needles, or Nano particles of catalytic materials having a band gap of about 3±1 eV); one or more optional chemical substance (such as Hydrogen peroxide, tablets of Alkali percarbonates or Alkali perborates); and assorted combinations and permutations thereof. The apparatus typically includes a chamber with an inlet unit for air and treatment agents and an outlet unit for exhaust. A currently preferred air inlet system is also adapted to deliver air at a desired % relative humidity. An operable exhaust unit may further compromise a Hydroxyl radical and/or ozone destruction unit, and may be catalytic. The apparatus may further comprise a power source and one or more electronic module to control all the functions.

Since an effective sterilizing agent includes hydroxyl radicals, a goal is to maximize production of hydroxyl radicals. Radical generation can be accomplished via radiating Alkali percarbonates or Alkali perborates. It has been discovered that a Fenton or photo-Fenton reactor can be employed to great effect to introduce hydroxyl radicals into a chamber. The Fenton catalyst (Fe, catalyst) with Hydrogen peroxide or Alkali percarbonate or Alkali perborate can be used to provide Hydroxyl radicals in a treatment chamber.

EXAMPLE EXPERIMENT

The following example illustrates a simple embodiment of this invention. A treatment chamber embodied as an Aluminum box of dimensions 20 inches long, by 15 inches wide and 3.75 inches deep was used as a sterilization chamber for this experiment. The Biological Indicator called G. Sterothermophilus was used for determining the efficacy of sterilization. The total Sterilization Chamber volume was approximately 1,800 Cubic inches. The Ozone generator of 3 gms per hour was used as sterilant along with 3% Hydrogen Peroxide solution to generate Hydroxyl radicals. First, the Biological Indicator mentioned above was placed in the chamber in solution form. The chamber was tightly closed. The ozonator was activated with air flowing at a rate of 7 liters per minute. The ozonated air was then mixed with Hydrogen Peroxide vapor generated by a nebulizer. This approach generated Hydroxyl radicals in the Sterilization Chamber once believed to be set forth by the following reaction:

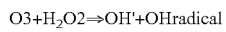

$O3+H_2O2 \Rightarrow OH'+OH radical$

According to world wide web://pubs.acs.org/doi/abs/10.1021/es100277d "The new mechanism of the peroxone process considers the formation of an ozone adduct to $HO_2^-$, $HO_5^-$ that decomposes into $HO_2.+O_3.^-$ and $2O_2+OH^-$ the latter accounting for the low .OH efficiency."

In any case, these Hydroxyl radicals have 15 times more power than Ozone as a sterilent. The process was activated for approximately 8 to 10 minutes. The result showed 100% sporocidal Sterilization. After Sterilization Cycle, the sample was left in incubation for 7 days. After 7 days we did not observe not even one spore colony.

This is just one example. This invention has many other innovative approaches to generate Hydroxyl generation without Ozone Generator and Solution of Hydrogen Peroxide. Also the approaches mentioned in this disclosure are more effective and less cumbersome than commercially available options.

While the invention has been described in particular with reference to certain illustrated embodiments, such is not intended to limit the scope of the invention. The present invention may be embodied in other specific forms without departing from its spirit or essential characteristics. The described embodiments are to be considered only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
a first chamber defining a volume in which to receive one or more object to be treated; and
a source of Hydroxyl radicals configured and arranged to introduce Hydroxyl radicals as a first treatment agent inside said first chamber; wherein:
said source of Hydroxyl radicals is operable to establish a Hydroxyl radical concentration of between about 50 ppm and about 10,000 ppm in said first chamber; and
a second treatment agent disposed in said chamber, said first and second treatment agents to deodorize, disinfect, and/or sterilize said one or more object; and
a tablet dispenser structured to dispense a chemical compound into said first chamber to introduce said second treatment agent into said first chamber.

2. The apparatus according to claim 1, wherein:
said source of Hydroxyl radicals comprises structure configured to urge flow of Hydrogen Peroxide over a surface-mounted catalyst substance in the presence of UV light.

3. The apparatus according to claim 2, wherein:
said catalyst substance comprises an anatase Titanium Oxide Nano needle array plate.

4. The apparatus according to claim 2, wherein:
said catalyst substance comprises Nano Gallium Nitride tubular or wire structures.

5. The apparatus according to claim 2, further comprising:
a source of Ozone structured to introduce Ozone molecules into said first chamber as said second treatment agent.

6. The apparatus according to claim 1, wherein:
said source of Hydroxyl radicals is configured to produce Hydroxyl radicals exterior to said first chamber.

7. The apparatus according to claim 1, wherein:
said source of Hydroxyl radicals is configured to produce Hydroxyl radicals at a UV irradiated inside surface of said first chamber.

8. The apparatus according to claim 1, wherein:
said source of Hydroxyl radicals comprises a Fenton reactor.

9. The apparatus according to claim 8, further comprising:
a source of Ozone structured to introduce Ozone molecules into said first chamber as said second treatment agent.

10. The apparatus according to claim 1, wherein:
said apparatus is structured to permit treating both inside and outside surfaces of tubular elements having a length.

11. The apparatus according to claim 10, further comprising:
a second chamber structured to communicate gasses to said first chamber through a lumen in a tubular object to be treated.

12. The apparatus according to claim 10, further comprising:
a Hydrogen Peroxide bath disposed inside said first chamber; and
an Ozone source configured and arranged to bubble gas containing Ozone through said bath to permit bubble travel through a lumen of an object to be treated inside said first chamber.

13. The apparatus according to claim 10, further comprising:
a vacuum disposed in communication through a first flow control device to said first chamber; and
the source of Hydroxyl radicals disposed in communication to said first chamber through a second flow control device.

14. The apparatus according to claim 1, wherein:
said apparatus is sized and constructed to permit transporting the treatment device through an opening of about 4 feet in width, and about 6 feet in height to permit operation of said apparatus at point-of-use of objects to be treated by said apparatus.

15. The apparatus according to claim 14, wherein:
said apparatus is sized and constructed to permit transporting said apparatus through an opening of about 4 feet in width, and about 6 feet in height.

16. The apparatus according to claim 1, wherein:
said chemical compound comprises alkali percarbonate or alkali perborate, or a combination thereof, in tablet form.

17. The apparatus according to claim 1, wherein:
said source of Hydroxyl radicals comprises a nebulizer arranged to introduce a mix of gasses into said first chamber, said mix of gasses comprising nebulized Hydrogen Peroxide and Ozonized air.

18. The apparatus according to claim 17, further comprising:
a source of Hydrogen Peroxide in fluid communication with said nebulizer; wherein
concentration of said Hydrogen Peroxide is between about 5% and about 50% by weight.

19. The apparatus according to claim 18, wherein:
said Hydrogen Peroxide also contains Silver Nitrate or Silver Citrate between about 0.05% to about 5% by weight.

* * * * *